United States Patent [19]

Hagen et al.

[11] Patent Number: 4,511,393
[45] Date of Patent: Apr. 16, 1985

[54] 3-CHLORO-8-CYANOQUINOLINES AND THEIR USE FOR CONTROLLING UNDESIRABLE PLANT GROWTH

[75] Inventors: Helmut Hagen, Frankenthal; Jüergen Markert, Mutterstadt; Rolf-Dieter Kohler, Edingen-Neckarhausen; Bruno Wuerzer, Otterstadt, all of Fed. Rep. of Germany

[73] Assignee: BASF Aktiengesellschaft, Fed. Rep. of Germany

[21] Appl. No.: 477,964

[22] Filed: Mar. 23, 1983

[30] Foreign Application Priority Data

Mar. 25, 1982 [DE] Fed. Rep. of Germany ....... 3210979

[51] Int. Cl.³ .................... A01N 43/48; A01N 43/40; C07D 215/20
[52] U.S. Cl. .......................... 71/92; 71/94; 544/128; 544/363; 546/167; 546/169; 546/171
[58] Field of Search ...................... 546/169, 171, 167; 71/92, 94; 544/128, 363

[56] References Cited

U.S. PATENT DOCUMENTS 3,764,681 10/1973 Dreikoru ............... 544/128
4,009,020 2/1977 Starke et al. ............. 71/94
4,036,963 7/1977 Gialdi et al. ............ 546/169

FOREIGN PATENT DOCUMENTS 1424359 2/1976 United Kingdom .

OTHER PUBLICATIONS

Akiya, S., in Chemical Abstracts, vol. 51, No. 15699i, (1957).

Primary Examiner—Donald G. Daus
Assistant Examiner—Cecilia Shen
Attorney, Agent, or Firm—Keil & Weinkauf

[57] ABSTRACT

3-Chloro-8-cyanoquinolines of the formula

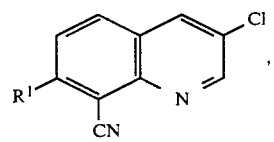

(I)

where $R^1$ is $-NR^2R^3$, and $R^2$ and $R^3$ are identical or different and are each hydrogen, $C_1$–$C_8$-alkyl, formyl, cyclohexyl, or phenyl, or together are tetramethylene or pentamethylene, and one methylene group in these radicals can be replaced by oxygen, nitrogen or $-N(CH_3)$, are used for controlling undesirable plant growth.

8 Claims, No Drawings

3-CHLORO-8-CYANOQUINOLINES AND THEIR USE FOR CONTROLLING UNDESIRABLE PLANT GROWTH

The present invention relates to 3-chloro-8-cyanoquinolines, herbicides containing these compounds as active ingredients, and a method of controlling undesirable plant growth with these active ingredients.

German Laid-Open Application DOS No. 2,322,143 and U.S. Pat. No. 2,661,276 disclose quinoline compounds which exhibit slight herbicidal activity.

We have found that 3-chloro-8-cyanoquinolines of the formula

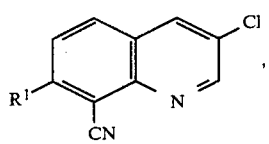

where $R^1$ is chlorine, bromine or $-NR^2R^3$, and $R^2$ and $R^3$ are identical or different and are each hydrogen, $C_1-C_8$-alkyl, $C_2-C_6$-alkenyl, $C_1-C_6$-hydroxyalkyl, $\omega$-dialkylamino-$C_1-C_6$-alkyl, formyl, cyclohexyl, phenyl or pyridyl, or together are tetramethylene or pentamethylene, and one methylene group in these radicals can be replaced by oxygen, nitrogen or $-N(CH_3)$, possess a more powerful herbicidal action than known quinoline derivatives.

In the formula I, $R^1$ is chlorine, bromine or $-NR^2R^3$, and $R^2$ and $R^3$ are each hydrogen, straight-chain or branched alkyl of 1 to 8, preferably 1 to 4, carbon atoms, straight-chain or branched alkenyl of 2 to 6, preferably 2 to 4, carbon atoms, straight-chain or branched hydroxyalkyl of 1 to 6, preferably of 1 to 4, carbon atoms, straight-chain or branched $\omega$-dialkylaminoalkyl, where alkyl is of 1 to 6 carbon atoms and dialkylamino is of 1 to 4 carbon atoms, formyl, cyclohexyl, phenyl or pyridyl, or $R^2$ and $R^3$ together may furthermore form a tetramethylene or pentamethylene radical in which one of the methylene groups can be replaced by oxygen, nitrogen or $-N(CH_3)$. Examples of such radicals are amino, dimethylamino, di-n-butylamino, n-butylamino, i-butylamino, di-n-propylamino, N-ethyl-N-n-butylamino, i-propylamino, N-methyl-N-phenylamino, cyclohexylamino, dicyclohexylamino, ethylamino, n-propylamino, n-hexylamino, n-octylamino, n-pentylamino, allylamino, diallylamino, (4-diethylamino-n-butyl)-amino, (3-dimethylamino-2,2-dimethyl-n-propyl)-amino, 2-hydroxyethylamino, dimethallylamino, diethylamino, diisopropylamino, methylamino, di-(2-hydroxyethyl)-amino, morpholino, tetramethyleneimino, pentamethyleneimino, 4-methyl-piperazin-1-yl, piperidin-1-yl and pyrrolidin-1-yl. Preferred compounds of the formula I are those in which $R^1$ is $-NR^2R^3$, $R^2$ is hydrogen and $R^3$ is $C_1-C_8$-alkyl, in particular $C_1-C_4$-alkyl, or cyclohexyl.

Compounds of the formula I in which $R^1$ is chlorine or bromine are obtained in a conventional manner by reacting a 3-chloro-8-dichloromethylquinoline derivative of the formula

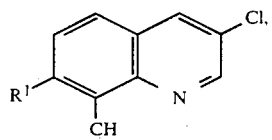

where $R^1$ is chlorine or bromine, with hydroxylamino hydrochloride and sodium formate in 100% strength formic acid at 100° C. The reaction time is from 10 to 20 hours.

Compounds of the formula I in which $R^1$ is $-NR^2R^3$ are obtained by reacting 3,7-dichloro-8-cyanoquinoline with an amine of the formula $HNR^2R^3$, where $R^2$ and $R^3$ have the above meanings. The reaction is carried out in a conventional manner, in the presence or absence of an inert organic solvent, at from 60° to 180° C., preferably from 80° to 110° C. The reaction time is from 1 to 30, usually from 10 to 20, hours. Suitable solvents are dimethylformamide, dimethylsulfoxide, alcohols, eg. methanol, and unsubstituted or substituted aromatics, eg. toluene, xylenes, chlorobenzene and dichlorobenzenes.

3-Chloro-7-amino-8-cyanoquinoline is obtained by reacting 3,7-dichloroquinoline with liquid ammonia, in the presence or absence of a solvent, in an autoclave. Where a solvent is used, this is preferably an alcohol.

The Examples which follow illustrate the preparation of the 3-chloro-8-cyanoquinolines of the formula I.

EXAMPLE 1

22.3 g of 3,7-dichloro-8-cyanoquinoline and 26 g of di-n-butylamine in 300 ml of methoxypropanol were refluxed for 12 hours, the solution was cooled, and the precipitated solid was filtered off under suction and recrystallized from a mixture of naphtha and toluene. 26 g of 3-chloro-8-cyano-7-di-n-butylaminoquinoline of melting point 112° C. were obtained. Yield: 82.5% of theory.

EXAMPLE 2

44.5 g of 3,7-dichloro-8-cyanoquinoline in 200 g of n-butylamine were heated at 80° C. for 14 hours, the solution was poured onto ice water and extracted with twice 100 ml of methylene chloride, the combined extracts were dried with $Na_2SO_4$ and evaporated down, the oily residue was treated with ether, and the precipitated solid was filtered off under suction. 39 g of 7-n-butylamino-3-chloro-8-cyanoquinoline of melting point 89° C. were obtained. Yield: 75% of theory.

EXAMPLE 3

110 g of 3,7-dichloro-8-cyanoquinoline in 500 ml of dimethylformamide were refluxed for 20 hours, the solution was cooled, an amount of water corresponding to half the volume of the solution was added, and the precipitated solid was filtered off under suction. 100 g of 3-chloro-8-cyano-7-dimethylaminoquinoline of melting point 174° C. were obtained. Yield: 87% of theory.

EXAMPLE 4

110 g of 3,7-dichloro-8-cyanoquinoline, 500 ml of methanol and 500 ml of liquid ammonia were heated at 150° C. for 10 hours in an autoclave. The pressure was let down, after which the discharged mixture was filtered under suction, and the solid was recrystallized from methylglycol, in the presence of active charcoal.

54 g of 7-amino-3-chloro-8-cyanoquinoline of melting point 246° C. were obtained. Yield: 53% of theory.

EXAMPLE 5

177 g of 7-chloro-8-methylquinoline and 1 g of azobisisobutyronitrile in 100 ml of dichlorobenzene were heated to 140° C. While chlorine was being passed in, the temperature was increased to about 175° C. The reaction was monitored by gas chromatography. After the reaction was complete, the solution was flushed with nitrogen, the major part of the solvent was distilled off, and the precipitated solid was filtered off under suction and washed with petroleum ether. 255 g of 3,7-dichloro-8-dichloromethylquinoline of melting point 154° C. were obtained. Yield: 80% of theory.

28.1 parts by weight of the 3,7-dichloro-8-dichloromethylquinoline thus obtained, 6.95 parts by weight of hydroxylamine hydrochloride and 13.6 parts by weight of sodium formate in 200 ml of formic acid and 60 ml of water were stirred for 12 hours at 100° C., the reaction solution was poured onto ice, the precipitated solid was filtered off under suction, washed neutral with water and dried. 19 parts by weight of 3,7-dichloro-8-cyanoquinoline of melting point 222° C. were obtained. Yield: 78.5% of theory.

The following compounds of the formula I may be prepared analogously:

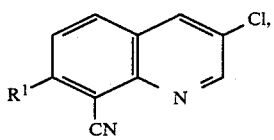

| No. | R$^1$ | M.p. [°C.] |
|---|---|---|
| 6 | —NH—i-C$_4$H$_9$ | 97 |
| 7 | —N(C$_2$H$_5$)$_2$ | 126 |
| 8 | —N(n-C$_3$H$_7$)$_2$ | 120 |
| 9 | —N(C$_2$H$_5$)(n-C$_4$H$_9$) | 110 |
| 10 | —N(morpholino) | 158 |
| 11 | —N(CH$_2$—CH=CH$_2$)$_2$ | 120 |
| 12 | —N(piperidino) | 125 |
| 13 | —N(pyrrolidino) | 252 |
| 14 | —N(4-methylpiperazino) | 136 |
| 15 | NH—i-C$_3$H$_7$ | 139 |
| 16 | N—methyl-N—phenylamino | |
| 17 | cyclohexylamino | 161 |
| 18 | dicyclohexylamino | |
| 19 | NH—C$_2$H$_5$ | |
| 20 | NH—n-C$_3$H$_7$ | 100 |
| 21 | NH—n-C$_6$H$_{13}$ | |
| 22 | NH—n-C$_8$H$_{17}$ | 105 |
| 23 | NH—(CH$_2$)$_4$—N(C$_2$H$_5$)$_2$ | |
| 24 | NH—CH$_2$—C(CH$_3$)$_2$—CH$_2$—N(CH$_3$)$_2$ | 122 |
| 25 | NH—CH$_2$CH$_2$OH | 172 |
| 26 | NH—n-C$_5$H$_{11}$ | 103 |
| 27 | NH—CH$_2$—CH=CH$_2$ | 170 |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below:

90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 16 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 14 is intimately mixed with 97 parts by weight of particulate kaolin. A dust is obtained containing 3% by weight of the active ingredient.

VII. 30 parts by weight of compound no. 14 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 5 is intimately mixed with 2 parts of the calcium salt of dodecylbenzenesulfonic acid, 8 parts of a fatty alcohol polyglycol ether, 2 parts of the sodium salt of a phenosulfonic acid-urea-formaldehyde condensate and 68 parts of a paraffinic mineral oil. A stable oily dispersion is obtained.

The active ingredients or agents may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved and the growth stage of the plants, and varies from 0.05 to 5 kg/ha and more, but is preferably from 0.1 to 3.0 kg/ha.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species.

For the postemergence treatment, the plants were first grown in the vessels to a height of from 3 to 15 cm, depending on growth form, before being treated. The active ingredients were emulsified or suspended in water as vehicle and sprayed through finely distributing nozzles. The rice plants were grown in a peat-enriched substrate. For this treatment, either plants which had been sown directly in the pots and grown there were selected, or plants which had been grown separately as seedlings and transplanted to the experiment vessels a few days before treatment. The application rates for postemergence treatment were 2.0 and 3.0 kg of active ingredient per hectare.

The pots were set up in the greenhouse—species from warmer areas at from 20° to 35° C., and species from moderate climates at 10° to 25° C. The experiments were run for up to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants were Amaranthus spp., Echinochloa crus-galli, Ipomoea spp., Lamium purpureum, Oryza sativa, Sesbania exaltata, and Solanum nigrum.

On investigations into herbicidal action on postemergence application at a rate of 3.0 kg/ha, for example compounds nos. 15, 17, 20 and 26 had a good herbicidal action on grassy plants, and compound no. 2, at 2.0 kg/ha, combated broadleaved unwanted plants very well.

Depending on the application method, the dosage rate and the weeds to be combated, the compounds of the formula I, or herbicidal agents containing them, may be used for example in the following crops:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guincensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |

-continued

| Botanical name | Common name |
| --- | --- |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the 3-chloro-8-cyanoquinolines of the formula I (or herbicidal agents containing them), either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

We claim:
1. A 3-chloro-8-cyanoquinoline of the formula,

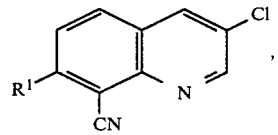

where $R^1$ is $-NR^2R^3$, and $R^2$ and $R^3$ are identical or different and are each hydogen, $C_1-C_8$-alkyl, $C_2-C_6$-alkenyl, $C_1-C_6$-hydroxyalkyl, $\omega$-dialkylamino-$C_1-C_6$-alkyl, formyl, cyclohexyl or phenyl, or together are tetramethylene or pentamethylene, and one methylene group in these radicals can be replaced by oxygen, nitrogen or $-N(CH_3)$.

2. A 3-chloro-8-cyanoquinoline of the formula I as defined in claim 1, where $R^2$ is hydrogen and $R^3$ is $C_1-C_8$-alkyl or cyclohexyl.

3. 7-n-Butylamino-3-chloro-8-cyanoquinoline.

4. A herbicide containing inert additives and an effective amount of 3-chloro-8-cyanoquinoline of the formula I as claimed in claim 1.

5. A herbicide containing inert additives and an effective amount of 3-chloro-8-cyanoquinoline as claimed in claim 2.

6. A herbicide containing inert additives and an effective amount of 7-n-butylamino-3-chloro-8-cyanoquinoline.

7. A herbicide containing inert additives and from 0.1 to 95 wt% of a 3-chloro-8-cyanoquinoline of the formula I as claimed in claim 1.

8. A process for combating the growth of unwanted plants, wherein the plants and/or their location are treated with a herbicidally effective amount of a 3-chloro-8-cyanoquinoline of the formula I as claimed in claim 1.

* * * * *